United States Patent [19]

Boozalis et al.

[11] 4,319,062

[45] Mar. 9, 1982

[54] ALLYL CHLORIDE PROCESS

[75] Inventors: Theodore S. Boozalis; John B. Ivy; Gordon G. Willis, all of Lake Jackson, Tex.

[73] Assignee: The Dow Chemical Company, Midland, Mich.

[21] Appl. No.: 896,866

[22] Filed: Apr. 17, 1978

Related U.S. Application Data

[63] Continuation-in-part of Ser. No. 710,934, Aug. 2, 1976, abandoned.

[51] Int. Cl.³ ............................................. C07C 17/10
[52] U.S. Cl. .................................. 570/220; 570/234; 570/241; 570/246; 570/252
[58] Field of Search .......... 260/654 H, 654 D, 658 R, 260/552 P; 570/220, 234

[56] References Cited

U.S. PATENT DOCUMENTS

| | | | |
|---|---|---|---|
| 2,748,176 | 5/1956 | Morris | 260/652 P |
| 2,952,713 | 9/1960 | Pallenberg et al. | 260/652 P |
| 3,006,974 | 10/1961 | De Prez | 260/654 H |
| 3,085,117 | 4/1963 | Brown et al. | 260/654 S |
| 3,914,167 | 10/1975 | Ivy et al. | 260/654 H |

*Primary Examiner*—Delbert E. Gantz
*Assistant Examiner*—Joseph A. Boska
*Attorney, Agent, or Firm*—A. C. Aneona

[57] ABSTRACT

An improved process for production of allyl chloride which comprises (1) thermally chlorinating propylene above 300° C., but below that at which substantial carbon formation is effected, (2) separating the allyl chloride from its by-products, (3) subjecting the unsaturated compounds in said by-products to a low temperature chlorination, (4) separating the 1,2-dichloropropane from the products of said low temperature chlorination, and (5) passing said 1,2-dichloropropane to a cracking furnace. The effluent from the cracking furnace can be recycled to the allyl chloride finishing system by adding it to the high temperature propylene chlorination reactor effluent. Reaction temperatures are optimized to eliminate problems caused by carbon formation in the high temperature chlorination reactor, while overall yields of allyl chloride are increased and effluents which are ecologically and economically undesirable are reduced.

9 Claims, No Drawings

ALLYL CHLORIDE PROCESS

CROSS-REFERENCE TO RELATED APPLICATION

This is a continuation-in-part of our copending application Ser. No. 710,934, filed Aug. 2, 1976, now abandoned.

BACKGROUND OF THE INVENTION

Allyl chloride is a useful commercial chemical especially as an intermediate in the manufacture of epichlorohydrin and glycerine. The principal commercial method for making allyl chloride is the thermal chlorinination of propylene. The problem in this chlorination essentially is to mix propylene and chlorine at the elevated temperature rapidly enough to obtain reasonable yields of allyl chloride which, with good mixing and a high ratio of propylene to chlorine, may reach 80 percent. The principal remaining organic constituents of the reaction product are 1,2-dichloropropane (propylene dichloride) from the addition of chlorine to propylene, and 1,3-dichloropropene from the further chlorination of allyl chloride together with smaller amounts of mono-, di-, and trichlorinated $C_3$'s. Some of these compounds are useful per se, e.g., 1,3-dichloropropenes are widely used as nematocides and soil fumigants. Some of the by-products, however, must be removed and disposed of since they are not useful of themselves. The useful method of disposal is to use these by-products as a feed for the preparation of more highly chlorinated hydrocarbons or by burning them and recovering heat and the chlorine values as HCl. It would be desirable if the amounts of by-products could be reduced or the kind of by-products be controlled so that a better yield of the desired products is obtained and/or the disposition of by-products could be more easily and economically achieved.

Thermal cracking of saturated compounds to produce unsaturated compounds is a highly developed art. Dehydrogenations and dehydrohalogenations to give unsaturated compounds and hydrogen or a hydrohalide are well known as commercially useful processes. The thermal cracking of ethylene dichloride to give vinyl chloride and of ethane to give ethylene are two examples of many which could be cited. Although catalysts are sometimes employed in such reactions, the use of high temperatures alone is usually sufficient and most frequently employed. Chlorinated hydrocarbons which contain unsaturation also undergo dehydrochlorination under these conditions. The result can be the formation of triple bonded compounds which are highly unstable and which tend to decompose rapidly to form carbonaceous materials which plug process equipment and prevent efficient operation.

It has now been discovered that a combination of direct chlorination and cracking steps can be used in order to render these by-products more ecologically acceptable and/or useful in recycling to the process in order to improve the overall yield to allyl chloride or other desirable products and avoid carbon formation.

Chlorination of unsaturated chlorohydrocarbons can result in either addition to the double bond or hydrogen substitution depending on the reaction conditions. The substitution reaction is also possible with saturated chlorohydrocarbons. Since, for the purposes of the present invention, the addition reaction generally results in the formation of more desirable materials, it is advantageous to operate the chlorination step using reaction conditions to favor the addition reaction and/or minimize substitution. For example, the addition reaction is favored by chlorination at low temperatures and in the presence of catalysts such as $FeCl_3$, while substitution is favored by elevated temperatures and actinic radiation.

In the common commercial method for the manufacture of allyl chloride by the substitution chlorination of propylene the preferred temperature is approximately 500° C. At these temperatures carbonaceous materials are invariably formed. Various schemes have been advanced in the past to reduce carbon formation, but they have met with very limited success. These schemes have generally involved the use of reactor design or diluents to prevent "hot spots" in the reactor.

The carbon, once formed, causes numerous problems. For example, it eventually plugs the thermal chlorination reactor, which must then be shut down and cleaned. Carbon build-up on the walls of the reactor can lead to the production of increased amounts of undesirable by-products. Also, extremely small particles of carbonaceous material remain in the reactor effluent and are almost impossible to remove. These small particles tend to enter the plant finishing system where they cause many problems. It would be extremely advantageous if carbon formation in the thermal chlorination reactor could be prevented or at least greatly reduced.

SUMMARY OF THE INVENTION

In the process to produce allyl chloride by the high temperature chlorination of propylene the chlorination reactor is operated at a temperature above 300° C., but below that at which substantial carbon formation is effected. The effluent from the thermal chlorination is fractionated to separate allyl chloride from the by-products. The by-products boiling above allyl chloride are then passed through a low temperature direct chlorination reactor where some or all of the unsaturated compounds present are reacted with chlorine in the absence of light to form higher boiling species. Prior to the low temperature chlorination certain of the unsaturated compounds, e.g., 1,3-dichloropropenes, in the stream may be removed for other uses. The products of the reaction between chlorine and the unsaturated chlorohydrocarbons are then removed from the by-product stream by simple distillation. The remainder, consisting primarily of 1,2-dichloropropane (PDC), is fed to a cracking furnace to produce a stream, the entire amount of which can be recycled to the system by introducing it into the effluent from the thermal chlorination reactor, recovering the by-product 1,2-dichloropropane as allyl chloride and other useful products. This avoids the problems caused by carbon formation in the high temperature chlorination reactor, while sustaining no significant yield loss as compared to the common high temperature commercial process.

DETAILED DESCRIPTION

As illustrated in Table I, the formation of carbon in the high temperature chlorination reactor is temperature dependent, and the amount of carbon formed increases rapidly after a certain critical temperature range is reached. Table I also shows that the allyl chloride yield is temperature dependent. Hence, in a conventional process, in order to obtain economically acceptable allyl chloride yields, the reactor temperature must be such that considerable carbon is also produced. It is, therefore, accepted commercial practical to sustain periodic production losses while the reactors are shut down for the removal of carbon.

As can be seen in Table I, substantially all the allyl chloride yield loss at the lower temperatures can be attributed to increased 1,2-dichloropropane formation. It is, therefore, obvious that if yield loss of allyl chloride to 1,2-dichloropropane can be averted, it would be possible to optimize allyl chloride yields at significantly lower temperatures from those in common commercial practice. This would offer the advantage of greatly reduced carbon formation in the thermal chlorination reactor. These lower temperatures also produce less undesirable by-products normally associated with higher reaction temperatures, such as acetylenic compounds and chlorinated six-carbon compounds.

In the present improved process the high temperature propylene chlorination reactor is operated in the temperature range at which carbon formation is negligible, i.e., 25°–75° C. below the temperature commonly considered economically feasible in a conventional process. This results in considerable decrease in allyl chloride yield, and a corresponding increase in PDC yield from the high temperature chlorination reaction. Preferably the high temperature chlorination is conducted at a temperature which results in a conversion of more than 7 percent of the propylene chlorinated to propylene dichloride (1,2-dichloropropane). A conversion of 7 to 20 percent is more preferred. However, with the improved process, total allyl chloride yields are not significantly reduced.

TABLE II

DISTILLATION CUT BOILING

| Below Allyl Chloride | | Above Allyl Chloride | |
|---|---|---|---|
| Component | Mole % | Component | Mole % |
| Propylene | 4 | Allyl Chloride | 3 |
| 2-Chloropropene | 60 | 3,3-Dichloropropene | 7 |
| 2-Chloropropane | 20 | 1,2-Dichloropropane | 25 |
| (c,t)1-chloropropene | 14 | 2,3-Dichloropropene | 5 |
| Allyl chloride | 2 | (c,t)1,3-dichloropropene | 54 |
| | | Others | 7 |

Typically, cuts boiling below (lights) and above allyl chloride (heavies) account for about 0.05 pound and 0.33 pound, respectively, for each pound of allyl chloride produced. As indicated above, some of the by-products of the allyl chloride process are themselves useful and, depending on the demand and/or the efficiency of their recovery from the by-product stream, will be removed and sold or used as starting materials in other processes. For example, 1,3-dichloropropene is customarily separated and sold as a soil fumigant since it frequently accounts for more than 50% of the bottoms of the distillation of the allyl chloride.

After removal of a soil fumigant fraction (principally 1,3-dichloropropenes) from the heavies from the allyl chloride process, there remains are stream which typically consists of from 60 to 80 mole percent 1,2-dichloropropane depending upon the efficiency of the soil fumigant distillation step. The remaining compo-

TABLE I

THERMAL CHLORINATION OF PROPYLENE

| Run Conditions | Run 1 | Run 2 | Run 3 | Run 4 | Run 5 |
|---|---|---|---|---|---|
| Reaction Temperature, °C. | 431 | 450 | 480 | 503 | 528 |
| Chlorine Preheat, °C. | 50 | 50 | 50 | 50 | 50 |
| Propylene Preheat, °C. | 200 | 200 | 200 | 200 | 200 |
| Reaction Pressure, psig | 35 | 35 | 35 | 35 | 35 |
| Contact Time, sec. | 2 | 2 | 2 | 2 | 2 |
| Chlorine Feed Rate, mole/hr. | 9.73 | 9.73 | 9.73 | 9.73 | 9.73 |
| Propylene Feed Rate, mole/hr. | 42.15 | 42.15 | 42.15 | 42.15 | 42.15 |
| Yield Based on Propylene Feed | % | % | % | % | % |
| 2-Chloropropene | 3.07 | 2.73 | 2.78 | 2.89 | 2.68 |
| 2-Chloropropane | 1.65 | 1.60 | 1.70 | 1.62 | 1.27 |
| cis-1-Chloropropene | 0.53 | 0.41 | 0.37 | 0.45 | 0.67 |
| trans-1-Chloropropene | 0.67 | 0.80 | 0.87 | 1.58 | 1.94 |
| 1-Chloropropane | 1.26 | 1.22 | 1.20 | 1.42 | 1.85 |
| Allyl Chloride | 70.49 | 71.60 | 77.31 | 80.08 | 72.08 |
| 2,2-Dichloropropane | — | — | — | — | 0.10 |
| Benzene | — | 0.07 | 0.10 | 0.13 | 0.67 |
| 1,1-Dichloropropane | 0.07 | 0.06 | 0.05 | 0.06 | 0.08 |
| 3,3-Dichloropropene | 0.52 | 0.55 | 0.60 | 0.50 | 0.34 |
| 1,2-Dichloropropane | 14.78 | 12.82 | 7.48 | 4.82 | 4.51 |
| 2,3-Dichloropropene | 0.67 | 0.74 | 0.55 | 0.50 | 0.56 |
| cis-1,3-Dichloropropene | 3.40 | 3.75 | 3.57 | 2.98 | 4.17 |
| trans-1,3-Dichloropropene | 1.88 | 2.59 | 2.58 | 2.09 | 3.50 |
| Trichloropropene | — | 0.01 | — | — | — |
| 1,2,3-Trichloropropane | 0.04 | 0.08 | — | — | — |
| Unknowns | 0.97 | 0.97 | 0.84 | 0.88 | 6.03 |
| Total | 100.0 | 100.0 | 100.0 | 100.0 | 100.0 |
| Propylene Conversion, % | 21.92 | 24.10 | 22.43 | 21.56 | 22.11 |
| Relative Carbon Formation | 0.6 | 1.4 | 4.7 | 10.9 | 26.6 |

Table II gives the principal components of typical distillation cuts from the effluent of the thermal chlorination reactor in a commercial allyl chloride process:

nents of this stream are primarily dichloropropenes some of which, e.g., 2,3-dichloropropene, are difficult to separate from the PDC by simple distillation. These unsaturates do not react sufficiently in the cracking step to prevent their excessive building-up in a recycle stream and in the entire finishing section of an allyl chloride plant.

In the present improved process the crude PDC stream is subjected to a low temperature chlorination step in order to eliminate the above described separation problems and to reduce the level of the unsaturates which might further dehydrochlorinate in the subsequent cracking step, giving rise to the undesirable acetylenic compounds referred to above.

Prior to the cracking step those products of the cold chlorination boiling above PDC are removed by simple distillation. The cracking step to which the remainder of the PDC fraction is sent then produces a more useful group of by-products in addition to the allyl chloride which improves the overall yield. The other compounds (especially HCl and the 1-chloropropenes) are either useful in themselves or may be recycled or treated separately.

In the present improved process the high temperature chlorination of propylene to allyl chloride is carried out at a temperature of from 425°–480° C. for optimum allyl chloride yield and minimum carbon formation. The optimum reaction temperature is somewhat dependent on a reactor design, but is the maximum temperature at which carbon formation is insignificant. The low temperature chlorination of the by-products of this reaction which boil above the desired product (allyl chloride), according to the present invention, is conducted at temperatures of from 0°–100° C., but preferably at a temperature within the range of from about 10° to about 50° C.

Pressure employed for the low temperature chlorination preferably is slightly above atmospheric. Operable pressure is within the range of about 14 to about 100 psi (0.9 to 6.8 atmospheres).

With respect to the chlorine employed, any amount sufficient to accomplish the desired conversion of the unsaturates is operable, but an amount approximately stoichiometric based on the unsaturates present is preferred. Less than stoichiometric amounts, although still operable, merely lessen the efficiency of the process. The upper limit is a practial one with the handling of excess chlorine being the principal deterrent.

To show the advantages of employing the present process improvement, the following examples are given:

EXAMPLE 1

A crude propylene dichloride stream obtained as a result of separation of a 1,3-dichloropropene fraction (for use as a soil fumigant) from the high boiling by-products of the commercial production of allyl chloride by the high temperature direct chlorination of propylene was metered to a 2-inch diameter glass, cylindrical, water-cooled reaction vessel at the rate of 400 cc/hr. The reactor was maintained at about 25° C. and at atmospheric pressure. It was also shielded to exclude light. The crude propylene dichloride entered the reaction vessel near its bottom where it was contacted with chlorine at the rate of 1.02 moles of chlorine per hour. Product was taken off near the top of the glass reactor at a point which allowed a liquid bed of approximately 1000 cc. No catalyst was added to the reactor, but the crude propylene dichloride obtained from the allyl chloride production facility contained about 12 ppm iron. Several hours of operation were allowed for the liquid bed composition to equilibrate, then a material balance run was made. Into the reactor were fed 931 grams crude propylene dichloride and 144 grams chlorine. During the same period 1062 grams liquid product and 10 grams unreacted chlorine were recovered. Table III gives the composition of the crude propylene dichloride before and after chlorination. As can be seen, the majority of the unsaturated components were reacted to form higher boiling material such as tetrachloropropanes. Only a small amount of the propylene dichloride was chlorinated under these conditions.

TABLE III

SELECTIVE CHLORINATION OF UNSATURATED COMPOUNDS IN ALLYL CHLORIDE BY-PRODUCT PROPYLENE DICHLORIDE

| | 18469-24-A | |
|---|---|---|
| Run No. Component | Feed Wt. % | Product Wt. % |
| 2-Chloropropane | 0.02 | 0.02 |
| cis-1-Chloropropene | 0.03 | — |
| trans-1-Chloropropene | 0.04 | — |
| Unknown | 0.11 | 0.07 |
| Allyl Chloride | 0.81 | — |
| Benzene | 0.37 | 0.32 |
| 1,1-Dichloropropane | 0.46 | 0.17 |
| 3,3-Dichloropropene | 4.59 | 0.37 |
| 1,2-Dichloropropane | 76.32 | 63.23 |
| 2,3-Dichloropropene | 12.07 | 1.79 |
| cis-1,3-Dichloropropene | 4.74 | 0.50 |
| trans-1,3-Dichloropropene | 0.44 | — |
| Heavies | — | 33.53 |

EXAMPLE 2

Table IV gives the results of thermal dehydrochlorination of propylene dichloride produced as a by-product of allyl chloride manufacture. Two runs were made under similar conditions. In Run 18599-7-A the furnace feed was obtained by simple distillation of crude by-product propylene dichloride after selective low temperature chlorination as illustrated in Example 1. For Run 18599-9-A, untreated propylene dichloride exactly as obtained from a commercial allyl chloride plant, was fed to the dehydrochlorination furnace. As can be seen, the material subjected to the chlorination step of Example 1 gave a significantly higher rate of dehydrochlorination and a greatly reduced rate of plugging.

TABLE IV

THERMAL DEHYDROCHLORINATION OF PROPYLENE DICHLORIDE

| Run Conditions | | | | |
|---|---|---|---|---|
| Reaction Temperature, °C. | | 570 | | |
| Reaction Pressure, psig | | 20 | | |
| Propylene Dichloride Feed Rate, cc/hr. | | 100 | | |
| Reactor | | 1.18" × 6' Inconel | | |
| Catalyst | | none | | |
| Contact Time, sec. | | 1.7 | | |

| | 18599-7-A | | 18599-9-A | |
|---|---|---|---|---|
| Run Number | Feed Mole % | Product Mole % | Feed Mole % | Product Mole % |
| Lights | 0.21 | 0.50 | 0.23 | 0.47 |
| 2-Chloropropene | — | 1.20 | — | 1.80 |
| cis-1-Chloropropene | — | 9.26 | — | 5.77 |
| trans-1-Chloropropene | — | 6.18 | — | 3.30 |
| Allyl Chloride | — | 24.39 | 1.44 | 15.08 |
| Benzene | 1.37 | 2.91 | 1.20 | 2.15 |
| 1,1-Dichloropropane | 0.23 | 0.11 | 0.46 | — |
| 3,3-Dichloropropene | 0.08 | 0.04 | 4.58 | 0.57 |
| 1,2-Dichloropropane | 95.89 | 51.71 | 74.25 | 50.09 |
| 2,3-Dichloropropene | 1.83 | 1.33 | 11.91 | 10.95 |
| cis-1,3-Dichloropropene | 0.39 | 0.48 | 5.13 | 5.05 |
| trans-1,3-Dichloropropene | — | — | 0.76 | 4.23 |
| Heavies | — | 1.89 | 0.04 | 0.54 |
| % PDC Converted | | 46.1 | | 32.5 |

TABLE IV-continued

THERMAL DEHYDROCHLORINATION OF PROPYLENE DICHLORIDE

| | | |
|---|---|---|
| Total Hours Operation Before Reactor Plugged | 88 | 18 |

EXAMPLE 3

Table V compares yields that can be obtained by the present improved process with yields obtained by a conventional process. Column 1 and 3 in Table V gives the yields, based on propylene converted, from a high temperature propylene chlorination reactor operated under similar conditions with the exception of reaction temperature. The relative carbon formation in the run at 450° C. (column 1) is considerably lower than that in the 500° C. run (column 3), but the allyl chloride yield is several percent less at the lower temperature. Column 2 shows yields that would be obtained at 450° C., at which temperature carbon formation is relatively low, when the 1,2-dichloropropane produced in the high temperature chlorination reaction is handled according to the improved process of the present invention, illustrated in Examples 1 and 2 above. Note that application of the present invention will result in improved allyl chloride yields, and a many-fold reduction of carbon formation.

TABLE V

| Run No. | 15266-14-5 | | 15266-14-8 |
|---|---|---|---|
| Run Conditions | | | |
| Reaction Temperature, °C. | 450 | | 500 |
| Chlorine Preheat, °C. | 50 | | 50 |
| Propylene Preheat, °C. | 200 | | 200 |
| Reaction Pressure, psig | 35 | | 35 |
| Contact Time, sec. | 2 | | 2 |
| Chlorine Feed Rate, mole/hr. | 11.99 | | 11.99 |
| Propylene Feed Rate, mole/hr. | 38.01 | | 38.01 |
| Yield Based on Propylene Fed | Col. 1 % | Col. 2 % | Col. 3 % |
| 2-Chloropropene | 2.69 | 3.04 | 2.71 |
| 2-Chloropropane | 1.41 | 1.41 | 1.10 |
| cis-1-Chloropropene | 0.52 | 3.27 | 0.50 |
| trans-1-Chloropropene | 0.60 | 2.45 | 1.13 |
| 1-Chloropropane | 1.07 | 1.07 | 1.07 |
| Allyl Chloride | 69.64 | 76.80 | 72.94 |
| 2,2-Dichloropropane | 0.27 | 0.27 | 0.09 |
| Benzene | 0.01 | 0.01 | 0.12 |
| 1,1-Dichloropropane | 0.10 | 0.10 | 0.08 |
| 3,3-Dichloropropene | 0.90 | 0.90 | 0.81 |
| 1,2-Dichloropropane | 12.11 | — | 7.89 |
| 2,3-Dichloropropene | 0.96 | 0.96 | 0.91 |
| cis-1,3-Dichloropropene | 4.44 | 4.44 | 4.86 |
| trans-1,3-Dichloropropene | 3.95 | 3.95 | 4.44 |
| Trichloropropene | 0.33 | 0.33 | 0.39 |
| 1,2,3-Trichloropropane | 0.44 | 0.44 | 0.21 |
| Unknowns | 0.56 | 0.56 | 0.75 |
| Propylene Conversion, % | 28.5 | 28.5 | 28.3 |
| Relative Carbon Formation | 1.4 | 1.4 | 10.9 |

We claim:

1. A process for producing allyl chloride which comprises combining the steps of (1) reacting chlorine with propylene at a temperature of from about 425° C. to 480° C. in order to produce a product a major portion of which is allyl chloride and in which by-product 1,2-dichloropropane constitutes more than 7 mole percent of said product, (2) separating allyl chloride from its higher boiling by-products, (3) subjecting at least a part of said higher boiling by-products to a low temperature chlorination with chlorine, (4) separating 1,2-dichloropropane from the products of said chlorination, (5) passing said 1,2-dichloropropane to a cracking furnace and (6) recovering allyl chloride from the effluent of said cracking furnace whereby the overall yield of allyl chloride from the process is increased and the formation of carbon from the thermal chlorination is essentially eliminated.

2. The process of claim 1 wherein no more than 20% of the product from the thermal chlorination is 1,2-dichloropropane.

3. The process of claim 1 wherein cis- and trans-1,3-dichloropropenes are removed from the higher boiling by-products separated in step 2 prior to the low temperature chlorination (step 3).

4. The process of claim 1 where a catalyst is employed in the low temperature chlorination reaction (step 3).

5. The process of claim 4 wherein the catalyst is $FeCl_3$.

6. The process of claim 1 wherein the low temperature chlorination is conducted at a temperature within the range of about 0° to 100° C.

7. The process of claim 1 wherein the low temperature chlorination is conducted at a temperature within the range of 10° to 50° C.

8. The process of claim 1 where the pressure is maintained within the range of 14 to 100 psi.

9. The process of claim 1 wherein at least a stoichiometric amount of chlorine is employed in the low temperature chlorination based on the amount of unsaturates present.

* * * * *